United States Patent
Choudary et al.

(12)

(10) Patent No.: US 6,384,285 B1
(45) Date of Patent: May 7, 2002

(54) PROCESS FOR THE PREPARATION OF 4'-ISOBUTYLACETOPHENONE

(75) Inventors: Boyapati Manoranjan Choudary; Mutyala Sateesh; Mannepalli Lakshmi Kantam; Kulluri Venkata Sri Ranganath; Kondapuram Vijaya Raghaven, all of Hyderabad (IN)

(73) Assignee: Council of Scientific and Industrial Research (IN)

( * ) Notice: Subject to any disclaimer, the term of this patent is extended or adjusted under 35 U.S.C. 154(b) by 0 days.

(21) Appl. No.: 09/537,522

(22) Filed: Mar. 29, 2000

(51) Int. Cl.[7] ............................................. C07C 45/46
(52) U.S. Cl. ........................................................ 568/319
(58) Field of Search ......................................... 568/319

(56) References Cited

U.S. PATENT DOCUMENTS 4,960,943 A * 10/1990 Botta et al.
5,227,529 A * 7/1993 Neuber et al.
5,817,878 A * 10/1998 Spagnol et al.

OTHER PUBLICATIONS

Andy et al. , "Acylation of 2–Methoxynaphthalene and Isobutylbenzene over Zeolite Beta", Journal of Catalysis (2000), 192 (1), p 215–223.*

* cited by examiner

Primary Examiner—Johann Richter
Assistant Examiner—Sikarl A. Witherspoon
(74) Attorney, Agent, or Firm—Samuels, Gauthier & Stevens

(57) ABSTRACT

The present invention relates to a process for the preparation of 4'-isobutylacetophenone from isobutylbenzene which comprises reactions isobutyl benzene with acetic anhydride as an acylating agent in the presence of a zeolite beta catalyst at a temperature ranges between 60 to 165° C. for 2–12 h separating the catalyst by filtration from the reaction mixture and recovering the product by a conventional method.

6 Claims, No Drawings

PROCESS FOR THE PREPARATION OF 4'-ISOBUTYLACETOPHENONE

FIELD OF THE INVENTION

The present invention relates to a process for 4'-isobutylacetophenone (4-IBAP) by Friedel-Crafts acylation of isobutylbenzene. More particularly, this invention relates to a process for the preparation of 4'-isobutylacetophenone (4-IBAP) from isobutylbenzene using acetic anhydride as an acylating agent in the presence of nanocrystalline, microcrystalline and metal exchanged zeolite beta catalysts.

BACKGROUND OF THE INVENTION

4'-isobutylacetophenone (4-IBAP) is an important intermediate for 2-(4-isobutylphenyl)propionic acid (trade name, ibuprofen), a well-known nonsteroidal anti-inflammatory, antipyretic and analgesic drug and also other medical drugs.

This invention particularly relates to an ecofriendly process for 4'-isobutylacetophenone (4-IBAP) from isobutylbenzene using acetic anhydride as an acylating agent and zeolite beta as catalyst dispensing the use of stoichiometric amounts of corrosive, toxic aluminium chloride and hydrogen fluoride as Friedel-Crafts reagents.

PRIOR ART REFERENCES

Reference may be made to a publication by Baddley et al., Journal of Chemical Society, 1956, 4943, wherein 4'isobutylacetophenone is prepared by the Friedel-Crafts acetylation of isobutylbenzene with acetyl chloride using aluminium chloride as catalyst. Reference may be made to a U.S. Pat. No. 3,385,886 wherein the production of ibuprofen the first step of the process is preparation of 4'isobutylacetophenone by the Friedel-Crafts acetylation of isobutylbenzene with acetyl chloride in the presence of aluminium chloride. The draw-backs in the above processes are the use of stoichiometric amounts of anhydrous aluminium chloride, an hazardous material that leaves large amount of solid wastes after the reaction and tedious separation process from the alumina gel to obtain the product.

Reference may be made to a Japanese patent publication (Early disclosure) No. 60[1985]-188,343, wherein 4'isobutylacetophenone is prepared by the acetylation of isobutylbenzene using acetyl fluoride as an acetylating agent, prepared by reacting acetic anhydride with hydrogen fluoride as a catalyst a combination of hydrogen fluoride and boron trifluoride. Reference may be made to U.S. Pat. Nos. 4,981, 995 and 5,068,448 wherein the production of ibuprofen, 4'isobutylacetophenone is prepared by the Friedel-Crafts acetylation of isobutylbenzene with acetic anhydride using hydrogen fluoride. The 4'isobutylacetophenone is an intermediate in a process for the production of ibuprofen. The draw-bracks in the above processes are hydrogen fluoride is extremely toxic, corrosive, generation of large amount of solid wastes after the reaction and need for industrially expensive equipment to work with hydrofluoric acid.

The inherent disadvantages in the use of conventional Lewis acid metal chlorides for Friedel-Crafts acylation are that they are non-regenerable and require more than stoichiometric amounts because of complexation with the carbonyl product formed. Work-up to decompose the resultant intermediate complex by hydrolysis forms a large amount of waste product and separation is lengthy and expensive.

Obviously, different approaches have been employed for the preparation of 4'-isobutylacetophenone. There was therefore a need for a process for the preparation of 4'-isobutylacetophenone which is simple to operate and can be carried out in a media which are not toxic and corrosive. Moreover the catalyst should be simple to separate and reusable

OBJECTS OF THE INVENTION

The main object of the present invention is a process for the preparation of 4'-isobutylacetophenone from isobutylbenzene which comprises reacting isobutyl benzene with acetic anhydride as an acylating agent in the presence of nanocrystalline, microcrystalline and metal exchanged zeolite beta catalysts at a temperature ranges between 60 to 165° C. for 2 to 24 hrs, separating the catalyst by filtration from the reaction mixture and recovering the product by a conventional method which obviates the drawbacks as detailed above.

Another object of the present invention is the use of the nano- and microcrystalline and metal exchanged nano- and microcrystalline zeolite beta as catalysts.

Still another object of the present invention is the metal ions selected for the exchange of nano- and microcrystalline zeolite beta are $Fe^{3+}$, $Zn^{2+}$, $Ce^{3+}$ and $La^{2+}$.

Still another object of the present invention is the use of acetic anhydride as an acylating agent.

Still another object of the present invention is the use of isobutylbenzene as the reaction solvent.

Still another object of the present invention is the ratio of isobutylbenzene and acylating agent is 5:1 to 1:5.

Still another object of the present invention is the quantity of the catalyst is 10 to 50% by weight with respect to the acylating agent, acetic anhydride.

Yet another object of the present invention is the reaction is effected at a temperature in the range of 60 to 165° C. for 2–12 h.

SUMMARY OF THE INVENTION

The novelty of the present invention lies in the use of nanocrystalline and microcrystalline and metal exchanged nano- and microcrystalline zeolite beta for the acylation of isobutyl benzene for the first time. Decrease in particle size of zeolite beta, enhances the density of acidic sites and surface area of zeolites, which are essential factors to increase the activity of acylation reaction. In fact the activity of these nano-and microcrystalline forms increases manifold over normal zeolites. As a result of this, the acylation of isobutyl benzene is effected successfully in reasonable yields for the first time. 4'-isobutylacetophenone is obtained by a simple process involving filtration of the catalyst from the reaction mixture and recovering the product by conventional methods.

DETAILED DESCRIPTION OF THE INVENTION

Accordingly, the present invention provides a process for the preparation of 4'-isobutylacetophenone, an important intermediate for ibuprofen, a widely used non-steroidal anti-inflammatory drug wherein the said process comprises reacting isobutylbenzene with acetic anhydride as an acylating agent in the presence of nanocrystalline, microcrystalline and metal exchanged zeolite beta catalysts at a temperature ranges between 60 to 165° C. for 2–24 h separating the catalyst by filtration from the reaction mixture and recovering the product by a conventional method.

In an embodiment of the present invention metal exchanged, nanocrystalline and microcrystalline zeolite beta are used as the catalysts.

In an embodiment of the present invention the particle size of nanocrystalline and microcrystalline zeolite beta are 10 nm to 100 nm and 1 μm to 50 μm.

In another embodiment of the present invention the metal ions selected for the exchange of nano- and microcrystalline zeolite beta are $Fe^{3+}$, $Zn^{2+}$, $Ce^{3+}$ and $La^{2+}$.

In yet another embodiment of the present invention acetic anhydride is used as an acylating agent.

In still another embodiment of the present invention the reaction is effected at a temperature in the range of 60 to 165° C. for 2–12 hrs.

In still another embodiment of the present invention the catalyst is separated by filtration from the reaction mixture.

SCIENTIFIC EXPLANATION

In the nano- and microcrystalline zeolite by the density of the acidic sites increases because of increased number of broken edges resulted from the broken aluminium silicate rings. The surface area of these particles is also increased due to reduction of the particle size of zeolites. The higher density of acidic sites eventually increases number of acyl cations generated in the reaction in the electrophilic substitution of the Freidel-Crafts acylation and thus enhances activity of the reaction. Thus the higher density of acid sites present in nano-, microcrystalline, metal exchanged zeolite beta are responsible for the Friedel-Crafts acylation of isobutyl benzene for the first time.

Nanocrystalline, microcrystalline and metal exchanged zeolite beta were prepared as described in example 1 and employed them in the acylation of isobutylbenzene with acetic anhydride as an acylating agent as described in examples.

The following examples are given by way of illustration of the present invention and therefore should not be construed to limit the scope of the invention.

EXAMPLE 1

Catalyst Preparation a) Zeolite Beta

Tetraethyl orthosilicate and aluminium nitrate of appropriate molar ratios to get desired ratio of Si/Al ranging from 5 to 100 were used. Water is added to tetraethylortho silicate and stirred. To this solution aluminium nitrate, nonahydrate in tetraethylammonium hydroxide solution is added dropwise by a pressure regulating funnel under stirring. After the addition, the solution is kept at 50° C. and later on kept at 135° C. in an autoclave for one week for crystallization. Then the solid was filtered and air dried. The resultant solid was calcined at 500° C.

b) Microcrystalline Zeolite Beta-I

Microcrystalline zeolite beta-I was obtained by mechanical disintegration of the zeolite beta obtained as described above (1 μm–10 μm, 95%).

c) Microcrystalline Zeolite Beta-II

Microcrystalline zeolite beta was synthesised with different particle size (5 μm to 50 μm, 85%) by decreasing ageing time to 48 hours instead of one week during the synthesis of zeolite beta according to the above procedure.

d) Nanocrystalline Zeolite Beta

Nanocrystalline zeolite beta was synthesised with different particle size (10 nm to 100 nm) from the homogenised solution prepared in the first step of zeolite beta which is kept for crystallisation at different times by decreasing ageing time to control the nucleation growth of zeolite during the synthesis. Then the solid were separated by centrifugation and resultant solid was washed with distilled water and dried at 100° C.

e) Metal Exchanged Zeolite Beta 10 g of zeolite beta as synthesised or microcrystalline zeolite beta having Si/Al-15 was subjected to an ion-exchange procedure by stirring with 1 wt % to 10 wt % metal chloride ($Ce^{3+}$, $Fe^{3+}$, $Zn^{2+}$ and $La^{2+}$) solution at 80° C. for 6 hours. The resultant zeolite was washed with deionised water and dried at 120° C. After that the metal exchanged zeolite was calcined at 500° C. for 6 hours.

f) $H^+$-exchanged Zeolite Beta

Zeolite beta is added to 1 Molar $NH_4Cl$ solution (10 ml/g zeolite), stirred at 60° C. for 6 hours and the resultant solid was washed with deionised water and dried at 120° C. After that ammonium exchanged zeolite was calcined at 500° C. to get $H^+$-exchanged zeolite beta.

EXAMPLE 2

A mixture of isobutylbenzene (40 mmol), acetic anhydride (10 mmol) and zeolite beta catalyst (0.5 g) were stirred in a round bottomed flask (50 ml) under nitrogen atmosphere at 130° C. temperature. After completion of the reaction (followed by G. C.), the reaction mixture was filtered and distilled the reaction mixture to obtain the crude product. Yield: 0.11 g

EXAMPLE 3

A mixture of isobutylbenzene (1.5 mol) acetic anhydride (0.375 mol) and microcrystalline zeolite beta-I catalyst (20 g) were stirred in a round bottomed flask (1 lit) under nitrogen atmosphere at 130° C. temperature. After completion of the reaction (followed by G. C.), the reaction mixture was filtered and distilled the reaction mixture to obtain the crude product. Yield 13.4 g

EXAMPLE 4

A mixture of isobutylbenzene (40 mmol), acetic anhydride (10 mmol) and microcrystalline zeolite beta-II catalyst (0.5 g) were stirred in a round bottomed flask (50 ml) under nitrogen atmosphere at 130° C. temperature. After completion of the reaction (followed by G. C.), the reaction mixture was filtered and distilled the reaction mixture to obtain the crude product. Yield: 0.42 g

EXAMPLE 5

A mixture of isobutylbenzene (40 mmol) acetic anhydride (10 mmol) and $H^+$-exchanged microcrystalline zeolite beta-I catalyst (0.5 g) were stirred in a round bottomed flask (50 ml) under nitrogen atmosphere at 130° C. temperature. After completion of the reaction (followed by G. C.), the reaction mixture was filtered and distilled the reaction mixture to obtain the crude product. Yield: 0.36 g

EXAMPLE 6

A mixture of isobutylbenzene (40 mmol) acetic anhydride (10 mmol) and $Fe^{3+}$-exchanged zeolite beta catalyst (0.5 g) were stirred in a round bottomed flask (50 ml) under nitrogen atmosphere at 130° C. temperature. After completion of the reaction (followed by G. C.), the reaction mixture was filtered and distilled the reaction mixture to obtain the crude product. Yield: 0.21 g.

EXAMPLE 7

A mixture of isobutylbenzene (40 mmol), acetic anhydride (10 mmol) and $La^{3+}$-exchanged zeolite beta catalyst (0.5 g) were stirred in a round bottomed flask (50 ml) under nitrogen atmosphere at 130° C. temperature. After completion of the reaction (followed by G. C.), the reaction mixture was filtered and distilled the reaction mixture to obtain the crude product. Yield: 0.26 g.

EXAMPLE 8

A mixture of isobutylbenzene (40 mmol), acetic anhydride (10 mmol) and $Ce^{3+}$-exchanged microcrystalline zeolite beta-II catalyst (0.5 g) were stirred in a round bottomed flask (50 ml) under nitrogen atmosphere at 130° C. temperature. After completion of the reaction (followed by G. C.), the reaction mixture was filtered and distilled the reaction mixture to obtain the crude product. Yield: 0.52 g.

TABLE I

Acylation of isobutyl benzene with acetic anhydride by various zeolite beta catalysts.

| Example No. | Catalyst | Time (h) | Isolated yield (%) |
|---|---|---|---|
| 2 | Zeolite beta | 8 | 6 |
| 3 | Microcrystalline beta-I | 6 | 20 |
| 4 | Microcrystalline beta-II | 3 | 25 |
| 5 | $H^+$ microcrystalline beta-I | 6 | 20 |
| 6 | $Fe^{3+}$-beta | 8 | 12 |
| 7 | $La^{3+}$-beta | 6 | 15 |
| 8 | $Ce^{3+}$-microcrystalline beta-II | 3 | 30 |

The main advantages of the present invention are:
1. A novel and ecofriendly process for the preparation of 4'-isobutylacetophenone.
2. The present process eliminates the use of corrosive and stoichiometric quantities of aluminium chloride.
3. Nanocrystalline, microcrystalline and metal exchanged zeolite beta have been used as catalysts for the acylation of isobutylbenzene for the first time.
4. Work-up procedure is simple.
5. The present process envisages no disposal problem as the catalyst can be used for several cycles. The catalyst was subjected to 4 recycles which displayed consistent activity.
6. The present process is environmentally safe since there is no disposal problem.
7. The process is economical.

What is claimed is:

1. A process for the preparation of 4'-isobutylacetophenone from isobutylbenzene which comprises reacting isobutyl benzene with acetic anhydride as an acylating agent in the presence of a zeolite beta catalyst at a temperature ranges between 60 to 165° C. for 2–24 h separating the catalyst by filtration from the reaction mixture and recovering the product by a conventional method.

2. A process as claimed in claim 1 wherein the zeolite beta catalyst is selected from nano crystalline, microcrystalline and metal exchanged zeolite beta.

3. A process as claimed in claim 1 wherein the particle size of and microcrystalline zeolite beta are 10 nm to 100 nm and 1 μm to 50 μm, respectively.

4. A process as claimed in claim 1 wherein metal ions selected for exchange are $Ce^{3+}$, $Zn^{2+}$, $Fe^{3+}$, and $La^{2+}$.

5. A process as claimed in claim 1 wherein acetic anhydride is used as an acylating agent.

6. A process as claimed in claim 1 wherein the reaction is effected at a temperature in the range of 60 to 165° C. for 2–24hrs.

* * * * *